(12) United States Patent
Nance et al.

(10) Patent No.: US 8,402,843 B2
(45) Date of Patent: Mar. 26, 2013

(54) DISSOLUTION ACTUATED SAMPLE CONTAINER

(75) Inventors: Thomas A. Nance, Aiken, SC (US);
Frank T. McCoy, Barnwell, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 361 days.

(21) Appl. No.: 12/735,317

(22) PCT Filed: Jan. 23, 2009

(86) PCT No.: PCT/US2009/000450
§ 371 (c)(1),
(2), (4) Date: Jun. 30, 2010

(87) PCT Pub. No.: WO2009/094193
PCT Pub. Date: Jul. 30, 2009

(65) Prior Publication Data
US 2010/0282004 A1    Nov. 11, 2010

Related U.S. Application Data

(60) Provisional application No. 61/062,063, filed on Jan. 23, 2008.

(51) Int. Cl.
*G01N 1/10* (2006.01)
(52) U.S. Cl. .................................................. 73/864.63
(58) Field of Classification Search ............... 73/864.63
See application file for complete search history.

(56) References Cited

U.S. PATENT DOCUMENTS

| 4,481,952 | A | 11/1984 | Pawelec |
| 5,139,654 | A | 8/1992 | Carpenter |
| 5,454,275 | A | 10/1995 | Kabis |
| 5,482,123 | A | 1/1996 | Collee |
| 6,276,220 | B1 | 8/2001 | Varhol |
| 2003/0121336 | A1 | 7/2003 | Hubbell et al. |

FOREIGN PATENT DOCUMENTS

| EP | 0 440 023 | 1/1991 |
| FR | 2 380 548 | 9/1978 |
| FR | 2 554 236 | 5/1985 |
| WO | WO 99/41201 | 8/1999 |
| WO | WO 02/102243 | 12/2002 |
| WO | WO 2005/046485 | 5/2005 |

OTHER PUBLICATIONS

PCT International Search Report (PCT/US2009/000450), Savannah River Nuclear Solutions, LLC. (4 pgs).

*Primary Examiner* — Hezron E Williams
*Assistant Examiner* — Nashmiya Fayyaz
(74) *Attorney, Agent, or Firm* — J. Bennett Mullinax, LLC

(57) ABSTRACT

A sample collection vial and process of using a vial is provided. The sample collection vial has an opening secured by a dissolvable plug. When dissolved, liquids may enter into the interior of the collection vial passing along one or more edges of a dissolvable blocking member. As the blocking member is dissolved, a spring actuated closure is directed towards the opening of the vial which, when engaged, secures the vial contents against loss or contamination.

5 Claims, 4 Drawing Sheets

US 8,402,843 B2

DISSOLUTION ACTUATED SAMPLE CONTAINER

RELATED APPLICATIONS

This application claims the benefit of U.S. Application Ser. No. 61/062,063, filed on Jan. 23, 2008, and which is incorporated herein by reference.

STATEMENT AS TO RIGHTS TO INVENTIONS MADE UNDER FEDERALLY SPONSORED RESEARCH AND DEVELOPMENT

This invention was made with Government support under Contract No. DE-AC09-96SR18500 awarded by the United States Department of Energy. The Government has certain rights in the invention.

FIELD OF THE INVENTION

This invention is directed towards a liquid sampling apparatus which may be used to obtain samples from a variety of environments including in situ sampling of ground water, remote sampling from hazardous environments such as proximity to radiation sources, and samples from hazardous waste drums.

BACKGROUND OF THE INVENTION

There are a variety of sample vials and apparatuses that may be used to sample a liquid at a desired depth and/or location. To avoid premature activation of the sampling vials, it is known to use mechanical linkages, electronic cables, pull cables, hydraulic lines, pneumatic lines, or other tripping mechanisms to open up a port or valve within a vial so as to collect a sample.

While such sampling apparatuses and methods have proven useful, the complexity and cost of the apparatus renders such apparatuses unsuitable for many applications. Further, with potentially hazardous or contaminated sampling locations, the control lines and communication lines needed to signal the sample valve port to open must then be cleaned before use in another location.

Accordingly, there remains room for variation and improvement within the art of valve controlled samplers.

SUMMARY OF THE INVENTION

It is an object of at least one embodiment of the present invention to provide for a liquid sample collection container, such as a vial, which may be lowered to the desired depth within a sample location and which thereafter automatically opens and closes following the intake of the desired sample. The remote opening and closing functions make use of dissolvable plugs, a first plug, when dissolved, allowing a sample to enter into the vial and a second dissolvable plug which functions as a stop member that, when dissolved, allows a spring loaded ball valve to seat against either a cap opening or the container opening, thereby providing a fluid tight seal to the sampling vial.

It is another aspect of at least one embodiment of the present invention to provide for a collection vial which may be lowered through a bore hole to a selected depth within a groundwater area to be sampled. Upon exposure to groundwater, a first plug is dissolved allowing entry of surrounding ground water into an interior of the vial. After collection of the groundwater or other supernate, a second plug stop member is dissolved thereby actuating a spring loaded closure which seals the vial and allows the recovery of the vial using a retrieval line attached to the sample container.

It is another aspect of at least one embodiment of the present invention to provide for a liquid sampler apparatus comprising: a collection container defining an opening; a plug positioned covering the opening, the plug being formed of a dissolvable material; a blocking member positioned beneath the plug and opposite the opening, the blocking member being formed of a dissolvable material, wherein when the plug is dissolved, liquids may flow around at least one side of the blocking member, thereby entering an interior of the collection container; a spring positioned within the collection container; and, a valve positioned between the spring and the blocking member wherein when the blocking member is removed, the spring seats the valve against the opening, thereby sealing the collection container.

It is another aspect of at least one embodiment of the present invention to provide for a process of sampling a liquid comprising the steps of: introducing a sealed container into a liquid to be sampled, the sealed container having an opening, a dissolvable seal in communication with the opening and a stop member positioned between the dissolvable seal and an interior of the container, the stop member blocking a spring actuated closure mechanism from engaging the opening; dissolving the seal while the container is within the sample liquid, thereby permitting a portion of the liquid to enter into an interior of the container; dissolving the stop member, following the step of dissolving the seal; actuating the closure mechanism within the container following the dissolution of the stop member; wherein the container, containing a sample of the liquid, has the closure mechanism engaging the opening, thereby securing the liquid contents within the container.

It is another aspect of at least one embodiment of the present invention to provide for a sampling vial comprising: a vial having an opening and defining an interior volume; a seal in communication with the opening and in further communication with an exterior of the vial, the seal being dissolvable when placed in a fluid to be sampled; a blocking member positioned opposite the seal; a closure member housed within the interior of the vial, the closure mechanism in operative engagement with the blocking member; an actuator for directing the closure member toward the opening; wherein when the blocking member is dissolved, the actuator forces the closure member against the opening thereby sealing the contents against loss or external contamination.

It is another aspect of at least one embodiment of the present invention to provide for a liquid sampler apparatus comprising: a vial having an opening and defining an interior volume; a cap operatively engaging the opening of the vial, the cap further defining an aperture therethrough; a seal in communication with the cap aperture, the seal being dissolvable when placed in a fluid to be sampled; a blocking member positioned beneath the seal and within an interior defined by the cap; a closure mechanism housed within the vial interior, the closure mechanism in operative engagement with the blocking member; an actuator for directing the closure mechanism toward the vial opening and the cap; wherein when the blocking member is dissolved, the actuator forces the closure mechanism against the cap aperture, thereby sealing the contents of the vial against loss or external contamination.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

FIGS. 1A through 1D are a series of perspective and sectional views illustrating schematically the operation of a dissolution actuated sample container according to an aspect of the present invention.

DESCRIPTION OF THE PREFERRED EMBODIMENT

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus, or process pathway. To avoid redundancy, detailed descriptions of much of the apparatus once described in relation to a figure is not repeated in the descriptions of subsequent figures, although such apparatus or process is labeled with the same reference numbers.

Figure 1A:
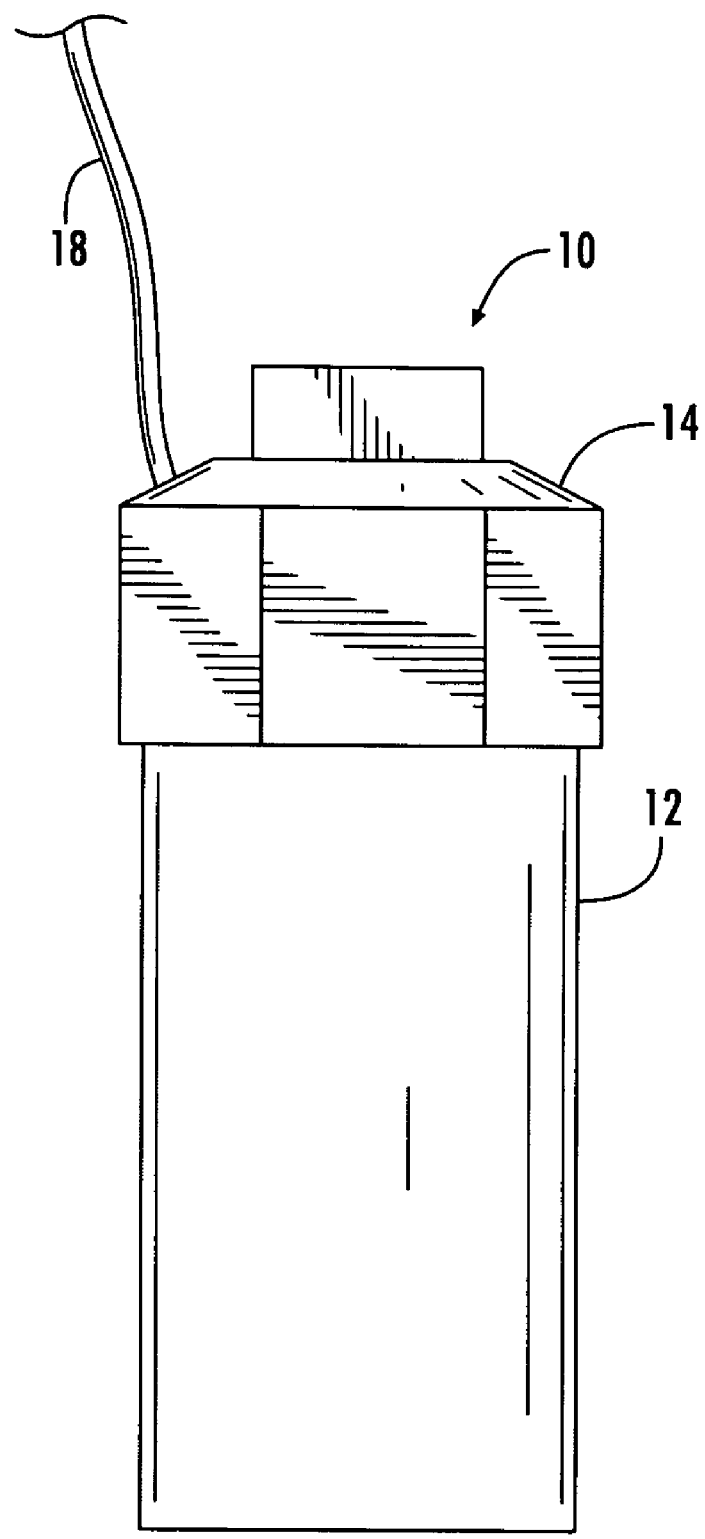

Set forth in FIG. 1A is a sample container 10 comprising a container seen in the form of a vial 12 and a cap 14. Cap 14 is designed to matedly engage vial 12 through an attachment mechanism such as a threaded connection. Attached to the cap 14 is a lift cable 18 which may be used to raise and lower the sample container 10.

Figure 1B:
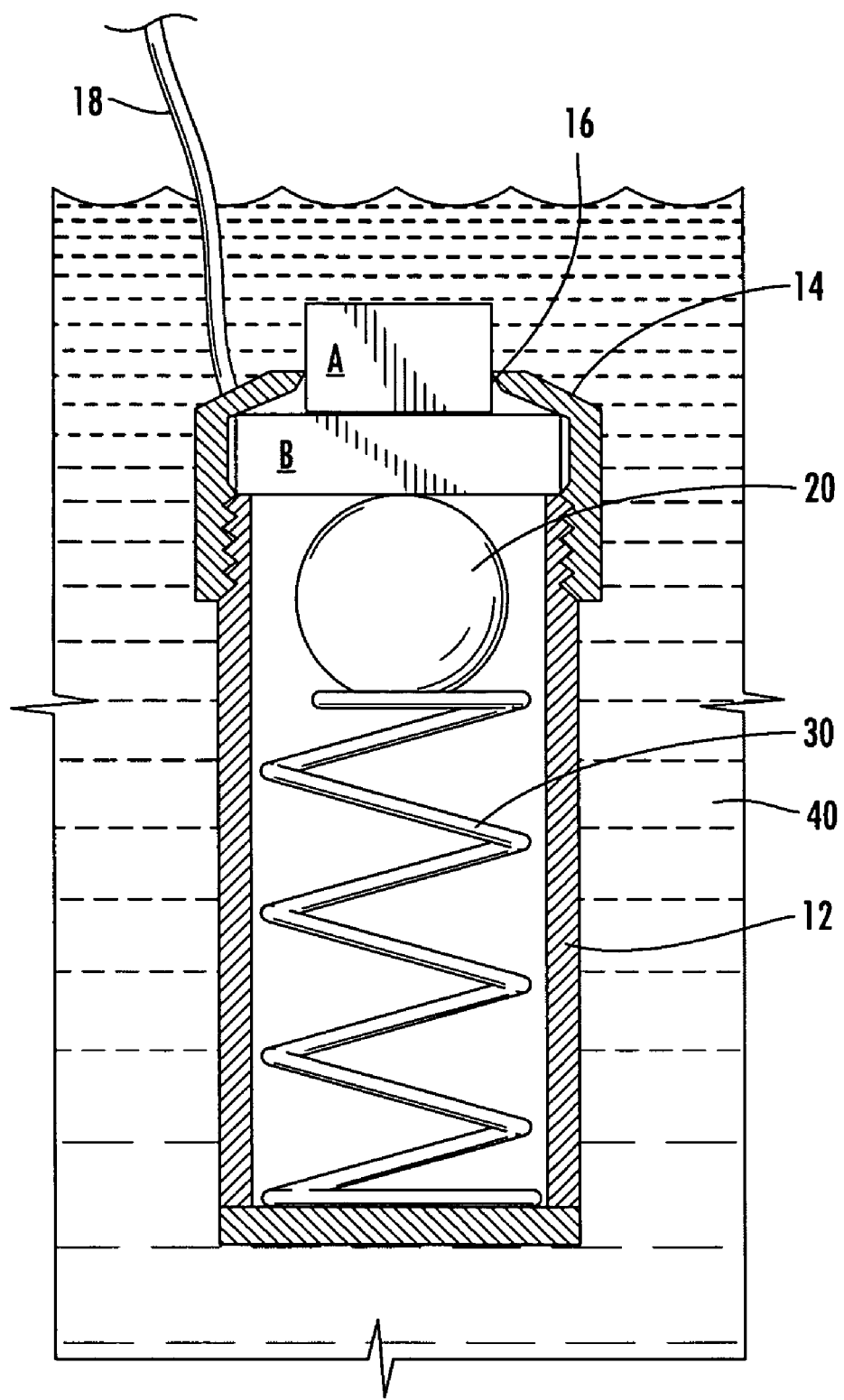
Figure 1C:
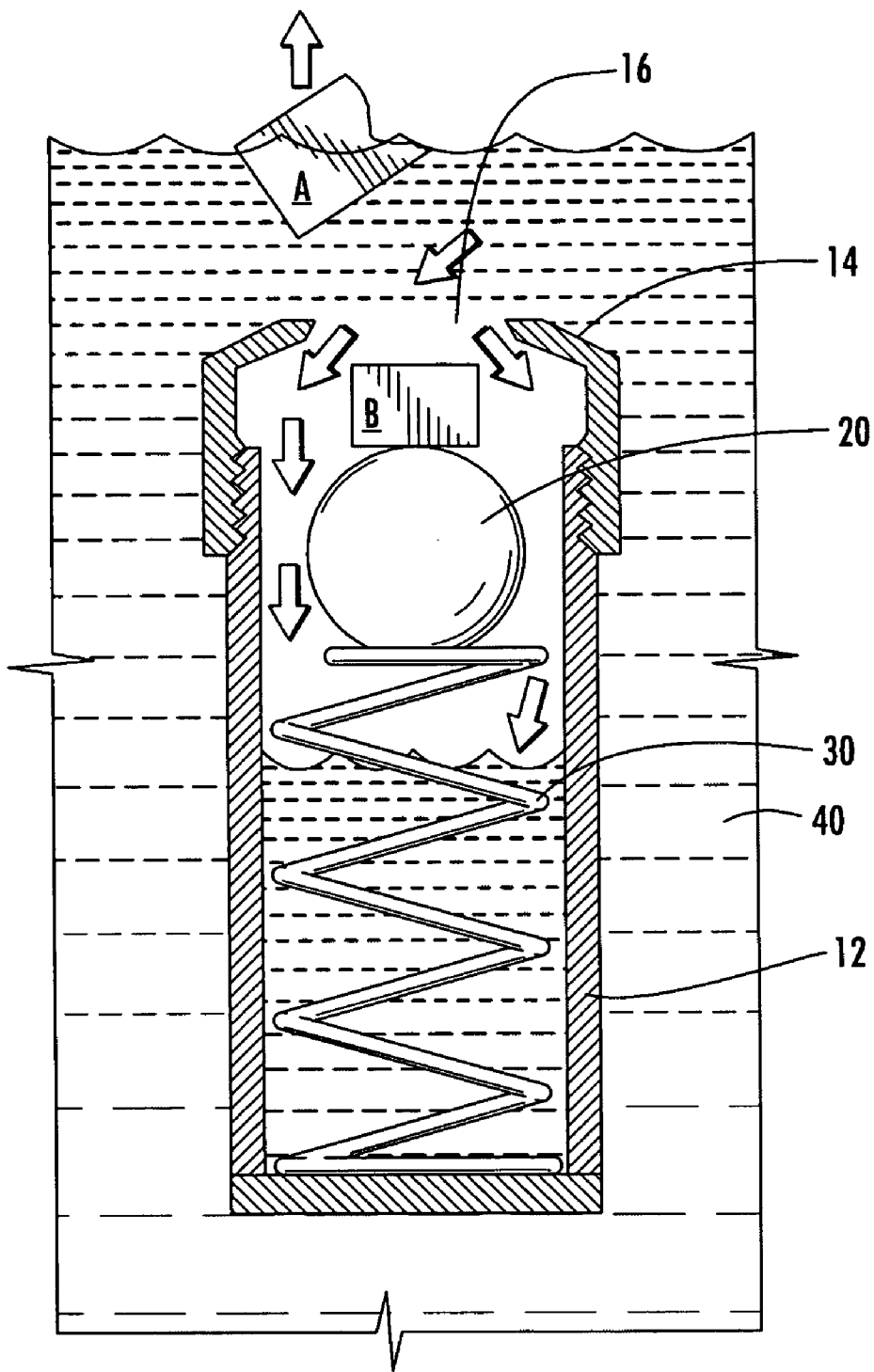
Figure 1D:
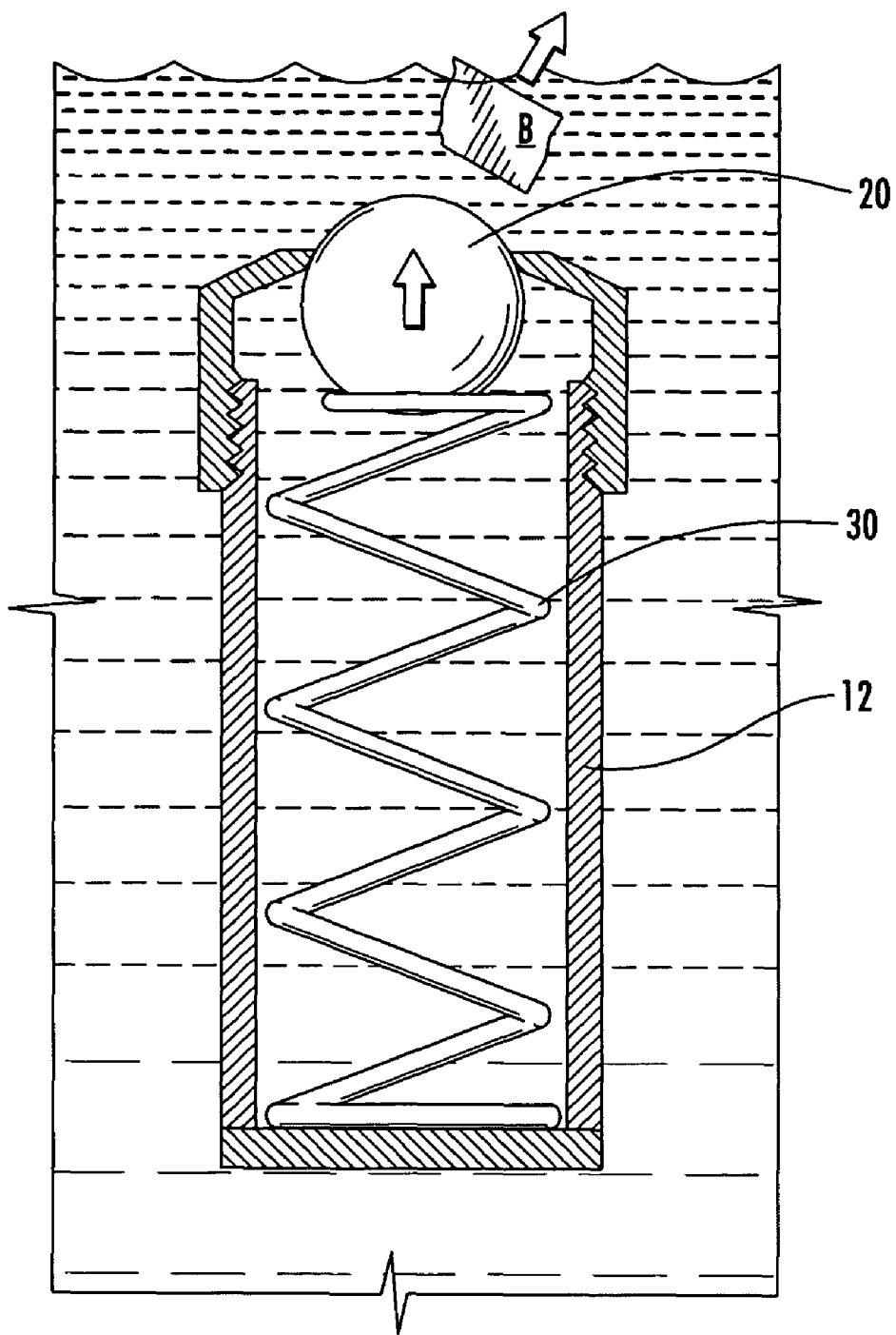

As further seen in the partial sectional views of FIG. 1B, cap 14 defines an opening 16 which initially has a plug A formed therein, plug A providing an initial liquid tight seal with respect to opening 16. Positioned within the interior of cap 14 is a second plug B which may be of a rectangular shape such that it has a length extending across the inner diameter of cap 14 but has a width which is less than its length and as depicted in FIG. 1C. Plug B will permit the entry of a fluid, such as a liquid 40, into the interior of vial 12 while initially retaining the ball check valve 20 in an open position.

As best seen in reference to FIG. 1C, plug B (shown at a viewing angle 90° displaced from FIG. 1B) holds in a tensioned fashion a ball check valve 20 which is responsive to a tensioned spring 30. As seen, the dimensions of Plug B allow for fluids to enter the interior of vial 12. Both plug A and plug B are made of a dissolvable material. Non-exemplary examples of dissolvable materials include hydroscopic materials such as a plug of compressed paperboard, gelatin, starch, and similar materials. In addition, certain water soluble crystalline materials could also be utilized such as sugar, salt, or sodium hydrogen carbonate. The latter ingredient is used in a variety of effervescent tablets for medicinal purposes and can be supplied in a plug-shape that will rapidly dissolve in the presence of water.

It is desirable to choose a plug material which is relatively inert with respect to the characteristics of the ground water being monitored. For instance, if a pH measurement or salinity characteristic are an important criteria, then a plug material which is inert with respect to altering pH or salinity is desirable. For instance, if a sample collection is being made to determine relative amounts of VOC in the groundwater sample, then a plug comprised of highly hydroscopic cellulosic fibers such as a pressed sheet of paper fibers or fines or similar material would serve as an effective plug. As the water interacts with the compressed hydroscopic cellulosic material, the plug will lose its integrity and be ejected. Any cellulosic remains of plug A or plug B present within the sampled contents may be filtered out or, depending upon the analytical technique used, be included in the analysis to the extent the plug material may have some binding affinity for one or more substrates of interest. However, knowing the composite material forming the plug allows for accurate identification of materials of interest by factoring in any influence the plug material may have.

In one embodiment of the present invention, plug B may be of a porous material that will admit liquid readily into the interior of vial 12. As the material making up plug B dissolves, and ball 20 seats against the cap 14, an adequate volume of liquid will have been collected within the interior of vial 12. Having a controlled porosity of plug material B helps prevent the premature ejection of plug B in circumstances where there was inadequate time for a sample to be collected.

Additional dissolvable plug materials which may be used include the dissolvable materials in U.S. Pat. No. 4,481,952 and WIPO application WO/2002/102243, which describe various types of dissolvable materials suitable for use in acidic environments. It is also envisioned that leachable, porous glass blocks may be used which, as the glass portion dissolves, the collection process proceeds as described above. For collections in heated environments, such as certain hazardous waste drums, water associated with nuclear reactors, and similar environments, the dissolvable plugs may be sensitive in part to temperature such that the ambient temperature at the collection site may be used to bring about dissolution of at least one of plug A or plug B.

Preferably, the material forming plug A and plug B is inert with respect to the characteristics and analysis being conducted of the collected supernate. For instance, an inert glass material may be ideal for environments where one does not wish to add a carbon source to the immediate environment which could affect the quality of subsequent readings.

While the nature of the plug may be varied, the sample container 10 operates on the principle that groundwater will bring about the dissolution of plug A which allows liquid to enter into opening 16 and flow past or through the width portion of plug B entering into the interior of vial 12. As the liquid enters vial 12, the resulting discharge of the air within the vial helps to propel plug A, or remnants of plug B, away from opening 16. Following the entry of liquid into the interior of vial 12, plug B begins to dissolve.

As seen in FIG. 1B, when plug B has sufficiently dissolved, the compressed spring 30 pushes ball 20 such that ball 20 is seated within opening 16. The release of spring 30 and ball 20 serves to eject the remaining plug portion B through opening 16. The compressive spring force from spring 30 against ball 20 seats ball 20 within opening 16 thereby sealing the sample container and preventing further entry or loss of the vial contents. The sample container, once sealed, permits only liquid from a desired depth in an exemplary groundwater collection environment to be present within vial 12. Once plug B has dissolved and the ball 20 is seated within opening 16, the sample container 10 may be removed without any altering of the contents by loss or entry of additional material.

Once removed, the sample container may be rinsed to remove any unwanted contaminants or hazardous materials and may be subsequently transported for analysis. If required for security during shipment, an overcap can be installed over the sample container to secure the cap 14 to vial 12.

If desired, cap 14 can be optional such that vial 12 has a shaped opening as opposed to a threaded opening. The opening may be sealed directly by Plug A with the opening 16 shaped to allow interaction between a blocking member Plug B and the opening as well as permitting the closure mechanism, such as ball 20, to form a fluid tight seal within the vial 12. Cap 14 and/or ball 20 may be formed of plastic, silicone, or other inert materials which lend themselves to forming tight seals.

It is also recognized that many types of closure mechanisms can be utilized with the present invention including spring actuated valves. It is understood that instead of a ball valve, a resilient rubber or silicone type plunger could be utilized which, when engaged with the closure opening, seals the container against further entry or loss of fluid contents.

To remove the contents, the threaded cap 14 may be removed to access the contents. Alternatively, ball 20 can be depressed down in the direction of the spring 30 which allows the contents of the vial to be emptied through opening 16.

Although preferred embodiments of the invention have been described using specific terms, devices, and methods, such description is for illustrative purposes only. The words used are words of description rather than of limitation.

It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

That which is claimed:

1. A liquid sampler apparatus comprising:
    a collection container defining an opening;
    a plug positioned covering said opening, said plug being formed of a dissolvable material;
    a blocking member positioned beneath said plug and opposite said opening, said blocking member being formed of a dissolvable material, wherein when said plug is dissolved, liquids may flow through said opening and around at least one side of said blocking member, thereby entering an interior of said collection container;
    a spring positioned within said collection container; and,
    a valve positioned between said spring and said blocking member wherein when said blocking member is removed, said spring seats said valve against said opening, thereby sealing said collection container.

2. A process of sampling a liquid comprising the steps of:
    introducing a sealed container into a liquid to be sampled, said sealed container having an opening, a dissolvable seal in communication with said opening and a stop member positioned between said dissolvable seal and an interior of said container, said stop member blocking a spring actuated closure mechanism from engaging said opening;
    dissolving the seal while the container is within the sample liquid, thereby permitting a portion of said liquid to enter into an interior of the container;
    dissolving said stop member, following the step of dissolving the seal;
    actuating said closure mechanism within said container following the dissolution of said stop member;
    wherein said container, containing a sample of said liquid, as said closure mechanism engaging said opening, thereby securing the liquid contents within said container.

3. The apparatus according to claim 1 wherein said container further defines a threaded cap, said threaded cap defining an opening covered by said plug.

4. The apparatus according, to claim 3 wherein said blocking member is positioned beneath said plug and within an interior of said threaded cap.

5. The apparatus according to claim 4 wherein said threaded cap has secured thereto a cable for raising and lowering said liquid sampler apparatus.

* * * * *